United States Patent
Gould

Patent Number: 6,080,179
Date of Patent: Jun. 27, 2000

[54] RESILIENTLY RETRACTING EXTERNAL NASAL DILATOR

[76] Inventor: David L. Gould, 7309 Murdy Cir., Huntington Beach, Calif. 92647

[21] Appl. No.: 09/222,222

[22] Filed: Dec. 29, 1998

Related U.S. Application Data

[63] Continuation-in-part of application No. 08/812,404, Mar. 5, 1997, Pat. No. 5,961,537.
[60] Provisional application No. 60/012,856, Mar. 5, 1996.

[51] Int. Cl.[7] .......................................................... A61F 5/08
[52] U.S. Cl. ...................................................... 606/204.45
[58] Field of Search ............................. 606/204.45, 199, 606/204.25; 604/304, 307, 308; 602/54, 58, 902, 12; 128/898

[56] References Cited

U.S. PATENT DOCUMENTS

| | | | |
|---|---|---|---|
| 3,426,751 | 2/1969 | Radewan | 606/204.45 |
| 5,383,891 | 1/1995 | Walker . | |
| 5,476,091 | 12/1995 | Johnson . | |
| 5,533,499 | 7/1996 | Johnson . | |
| 5,533,503 | 7/1996 | Doubek et al. . | |
| 5,538,500 | 7/1996 | Peterson . | |
| 5,546,929 | 8/1996 | Muchin . | |
| 5,611,333 | 3/1997 | Johnson . | |
| 5,611,344 | 3/1997 | Muchin . | |
| 5,653,224 | 8/1997 | Johnson . | |
| 5,669,377 | 9/1997 | Fenn | 606/204.45 |
| 5,685,292 | 11/1997 | Fenn . | |
| 5,706,800 | 1/1998 | Cronk et al. . | |
| 5,817,039 | 10/1998 | Rauning | 606/204.45 |

Primary Examiner—Michael Buiz
Assistant Examiner—Vikki Trinh

[57] ABSTRACT

A removably lined adhesive strip for foreshortening a nose and dilating the nasal passages of the nose. The strip is an external strip with two end portions. One end portion is fixed to a position on or beyond the tip of the nose, such as immediately beyond the tip of the nose and the other end portion is fixed to a position on the bridge of the nose. The strip may be integrally formed with or separate from a spring nasal dilator applied across the bridge of the nose and to the nostril of the nose. The strip may be used with or without such a spring nasal dilator. One preferred embodiment of the strip includes an end portion which is generally the shape of a diamond or arrowhead with rounded tips so as to generally reflect the shape of the tip of the nose or the shape of the nose immediately beyond the tip of the nose. A method for applying the strip includes first applying one end portion to a position on or beyond the tip of the nose and then applying the other end portion to the bridge of the nose. Further disclosed is a resiliently retractable strip which is first stretched, then slowly retracts over time to slowly lift underlying tissue in the outwardly direction. The resiliently retractable strip may be applied transversely across the bridge of the nose or up and down the bridge of the nose to lift the tip of the nose. A combination strip having first and second strips may be applied both transversely across the bridge of the nose and up and down the bridge of the nose.

16 Claims, 13 Drawing Sheets

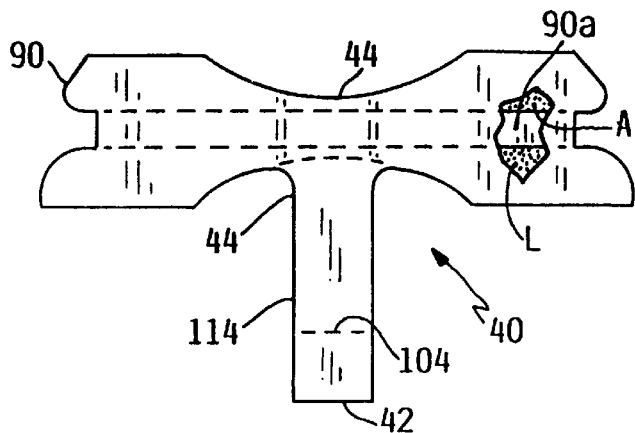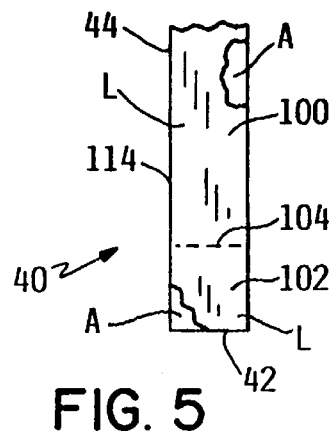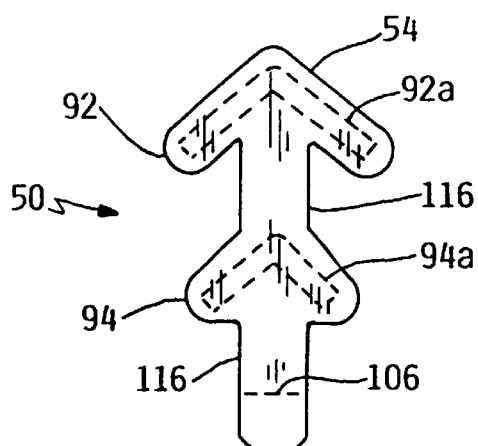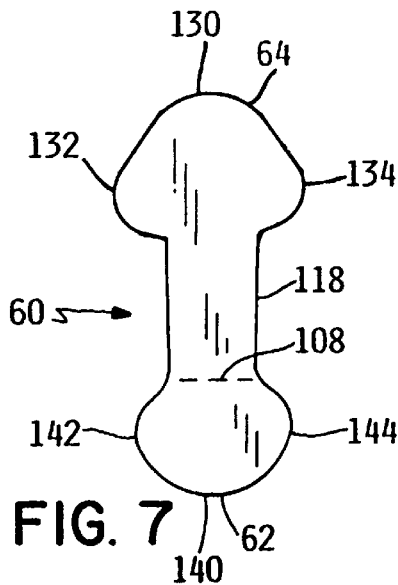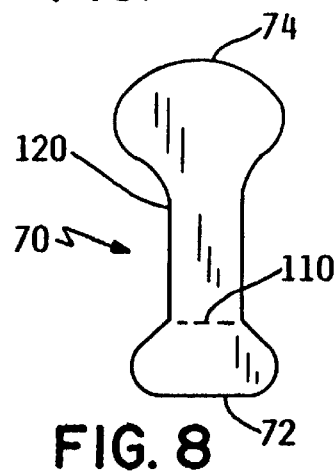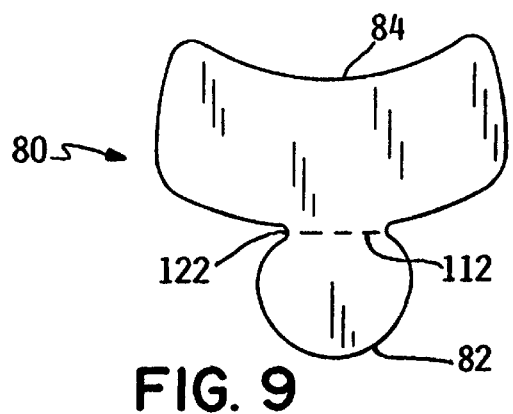

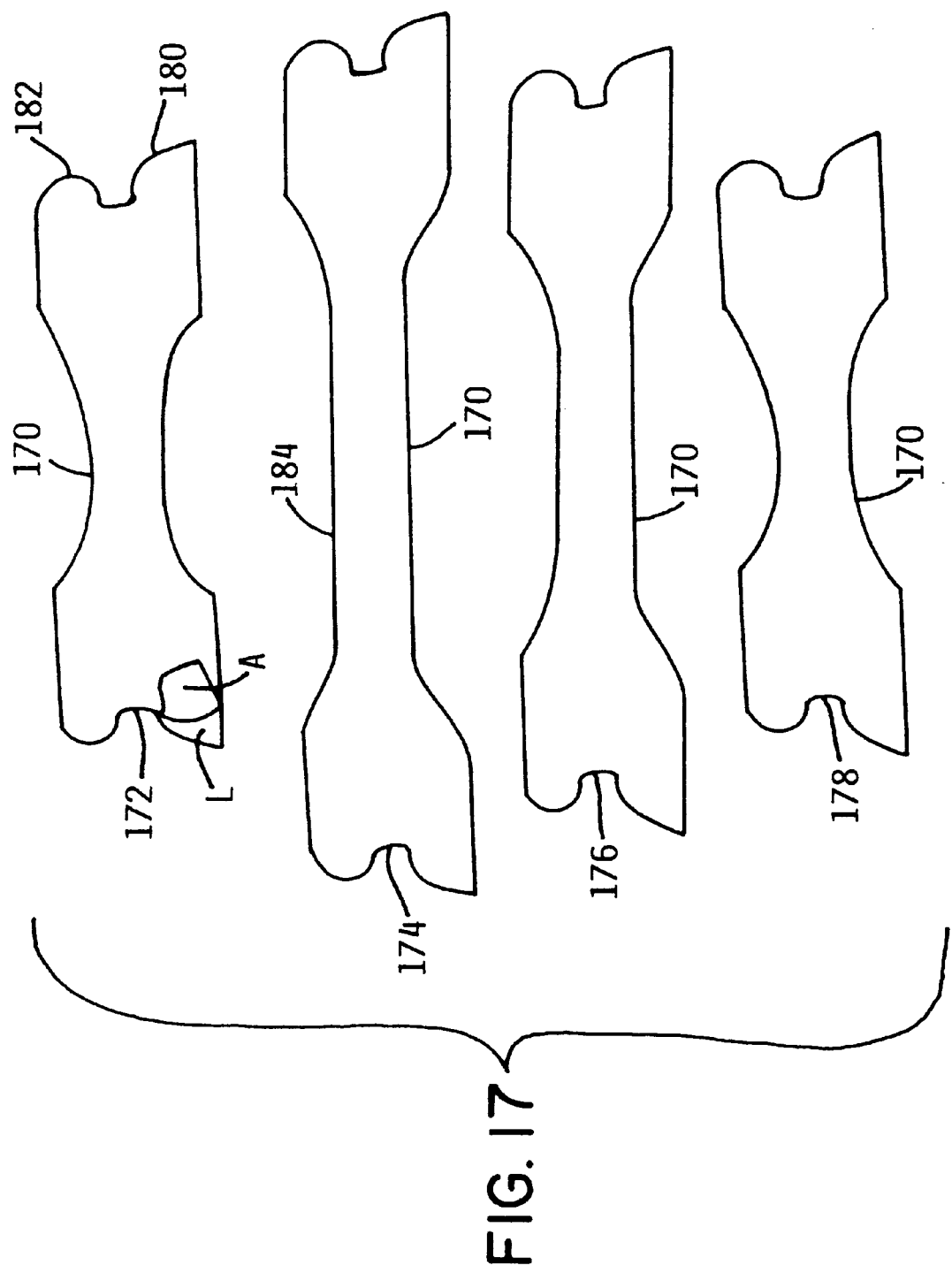

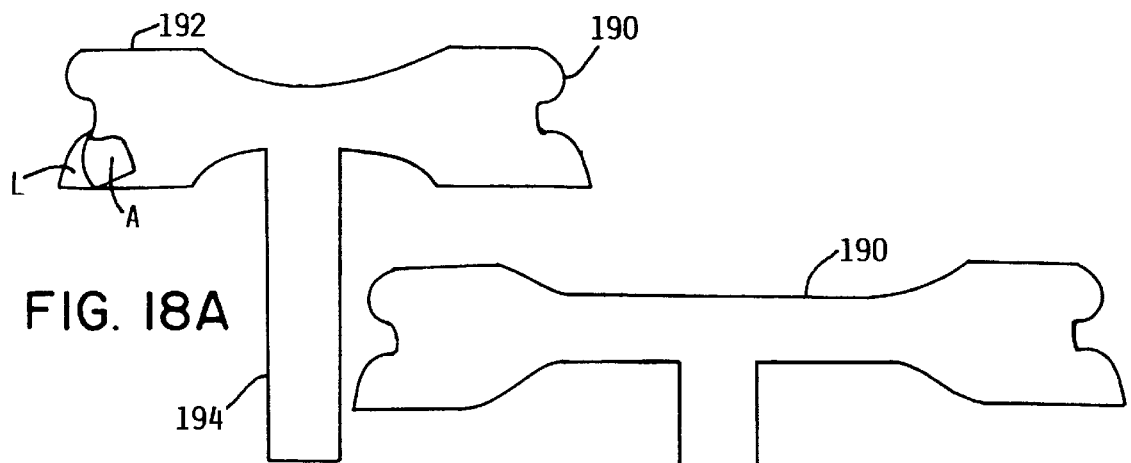
FIG. 18A
FIG. 18B
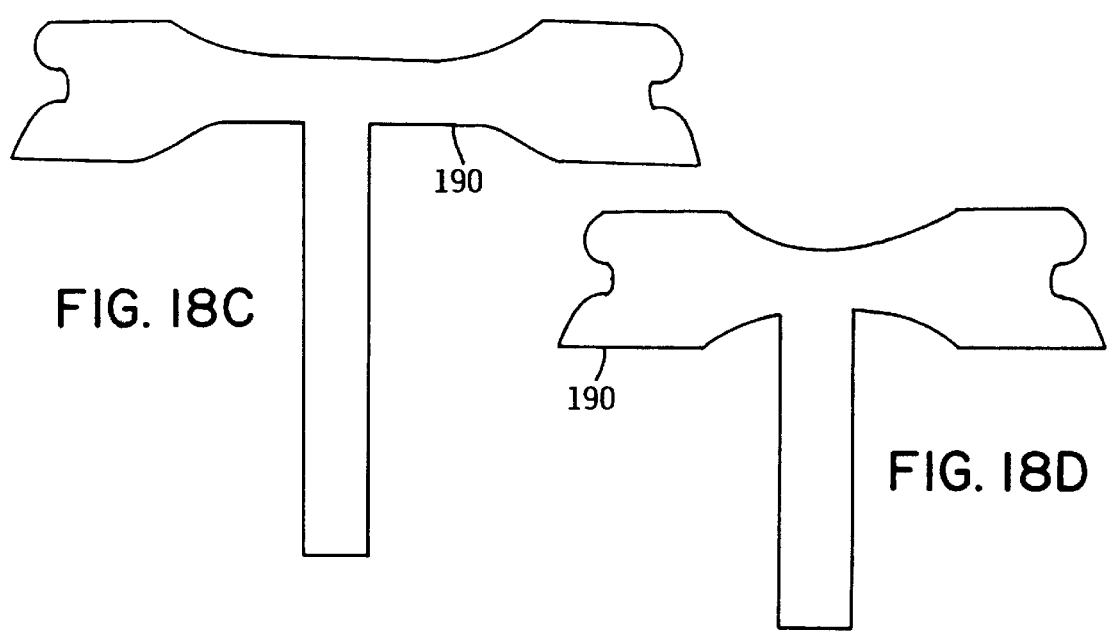
FIG. 18C
FIG. 18D

RESILIENTLY RETRACTING EXTERNAL NASAL DILATOR

This application is a continuation-in-part of U.S. patent application Ser. No. 08/812,404 filed Mar. 5, 1997, now U.S. Pat. No. 5,961,537 which in turn claimed the benefit under Title 35, United States Code § 119(e) of the United States Provisional Application No. 60/012,856 filed Mar. 5, 1996. Each of these applications are hereby incorporated by reference in its respective entirety into this continuation-in-part application.

BACKGROUND OF THE INVENTION

The present invention relates generally to external nasal dilators, and specifically to external nasal dilators that are resiliently retracting.

A spring nasal dilator is a strip of adhesive with a flat spring engaged therein. The spring nasal dilator is applied across the bridge of the nose and has portions which engage the nostrils. When the flat spring is thus bent across the bridge of the nose, it has a bias or tendency to return to its original flat shape and thereby pulls the skin or underlying tissue of the nose outwardly so as to dilate the nasal passages.

SUMMARY OF THE INVENTION

A general object of the present invention is to provide a unique external nasal dilator.

Another object of the invention is to provide an external nasal dilator that is uniquely resiliently retracting.

Another object of the invention is to provide an external nasal dilator that is resiliently retracting uniquely to its original unstretched configuration.

Another object of the invention is to provide an external nasal dilator that is uniquely formed from a rubber or elastomeric material or uniquely from a rubber based or elastomeric based material.

Another object of the invention is to provide a resiliently retracting external nasal dilator that is uniquely applied transversely across the bridge of the nose.

Another object of the invention is to provide a resiliently retracting external nasal dilator that is uniquely applied as a nose foreshortener.

Another object of the present invention is to provide a resiliently retracting nose strip to be applied either 1) transversely across the bridge of the nose or 2) as a nose foreshortener, i.e., generally vertically on the nose to run from between the nostrils up the bridge of the nose in the direction of the eyes or the middle of the eyes.

Another object of the present invention is to provide a resiliently retracting nasal dilator or nasal stabilizer that is formed from a resilient material that may be stretched in length and that which preferably resiliently retracts to a length close to its original length when in a stand alone configuration (i.e., when not on the nose) and, more preferably, retracts to its original length when in the stand alone configuration (i.e. when not on the nose). A nasal dilator that resiliently retracts to its original length provides a greater pulling force than a nasal dilator that resiliently retracts to a length close to its original length.

Another object of the present invention is to provide a resiliently retracting nasal dilator that includes an anchoring adhesive having a greater strength than the strength of the pulling force of the resilient retraction of the dilator.

Another object of the present invention is to provide a resiliently retracting nasal dilator having a sufficiently great resilient force to pull and stabilize nasal tissue and a sufficiently weak resilient force so as not to cause bleeding or tissue damage.

Another object of the present invention is to provide a unique method of stabilizing nasal tissue. When retracting, the nose strip pulls the outer skin in a sidewardly direction which in turn tends to pull its respective underlying tissue in a generally upwardly and oblique direction. This opens up the nasal passages and, at the very least, tightens and stabilizes the tissue of the nasal passages so as to minimize the chances of such tissue being drawn in when one breathes.

Another object of the invention is to provide for such a nose foreshortener a unique strip with two end portions. Each end portion has an inner adhesive face. One end portion is applied on or beyond the tip of the nose when the tip of the nose is compressed. The other end portion is applied on the bridge of the nose and serves as an anchor to keep the tip of the nose compressed. When the tip of the nose is maintained in such compressed state, the nasal passages are dilated and one may in turn breathe easier and take in more volume. When the tip of the nose is compressed, the alar cartilage, lateral nasal cartilage, cartilage of the nasal septum, and fibro-fatty tissue is compressed so as to dilate the nose. Further when the tip of the nose is so compressed, fibro-fatty tissue and lateral nasal cartilage vibration is minimized, so as to minimize snoring.

Another object of the invention is to provide for such a nose foreshortener a unique shape for one or more of the end portions. A preferred embodiment of the invention includes an end portion shaped generally like a diamond or arrowhead having rounded points. Such a shape generally reflects the shape of the tip of the nose.

Another object of the invention is to provide for such a nose foreshortener a unique liner. The liner includes two liner portions separated by a score. One liner portion has the shape of the end portion to be applied on or beyond the tip of the nose and this liner portion is removed first. The other liner portion is kept on the strip until the tip of the nose has been pushed up or compressed, thereby maintaining the adhesive for the anchor end in a clean nonoily state.

Another object of the invention is to provide for such a nose foreshortener a transversely oriented spring nasal dilator. The nose foreshortener may be integral with or formed of a separate piece from the transversely oriented spring nasal dilator.

Another object of the invention is to provide for such a nose foreshortener a strip which may be inverted. In other words, either end portion of the strip may be applied to either the tip of the nose or the bridge of the nose. Each of the end portions may have generally the same shape in such a case.

Another object of the invention is to provide a unique method for applying the nose foreshortener. It is preferred to first apply one end portion on or beyond the tip of the nose and to subsequently apply the anchoring end portion. The anchoring end portion hence is applied only once. Although the steps may be carried out in reverse order, such may result in taking off and reapplying the anchoring end so as to fix the other end portion at a comfortable position on or beyond the end of the nose.

These and further objects and advantages of the present invention will become clearer in light of the following detailed description of the illustrative embodiments of this invention described in connection with the drawings.

BRIEF DESCRIPTION OF THE DRAWINGS

The illustrative embodiments may be best described by reference to the accompanying drawings where:

FIG. 4 shows a top plan view of one embodiment of the present nose foreshortener formed integrally with a spring nasal dilator.

FIG. 5 shows a rear plan view of the nose foreshortener portion of the embodiment of FIG. 4 and illustrates two liner portions and a score between the liner portions.

FIG. 6 shows another embodiment of the invention and illustrates two inverted V-shaped spring nasal dilators.

FIG. 7 shows a top plan view of another embodiment of the present invention having two generally diamond shaped end portions.

FIG. 8 shows a top plan view of another embodiment of the present invention having blunted end portions.

FIG. 9 shows a top plan view of another embodiment of the present invention where one end portion is transversely oriented to extend across the bridge of the nose and where the other end portion, for placement immediately beyond the tip of the nose, is substantially immediately adjacent to the transversely oriented end portion.

FIG. 17 shows a transversely extending nasal strip in an unstretched configuration, a stretched configuration, a retracting configuration, and a fully retracted configuration.

FIG. 18A shows a combination nasal strip in an unstretched configuration.

FIG. 18B shows the nasal strip of FIG. 18A in a stretched configuration.

FIG. 18C shows the combination nasal strip of FIGS. 18A and 18B in a retracting configuration.

FIG. 18D shows the combination nasal strip of FIGS. 18A, 18B and 18C in a fully retracted configuration.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood. Where used in the various figures of the drawings, the same numerals designate the same or similar parts.

DESCRIPTION

Figure 13:
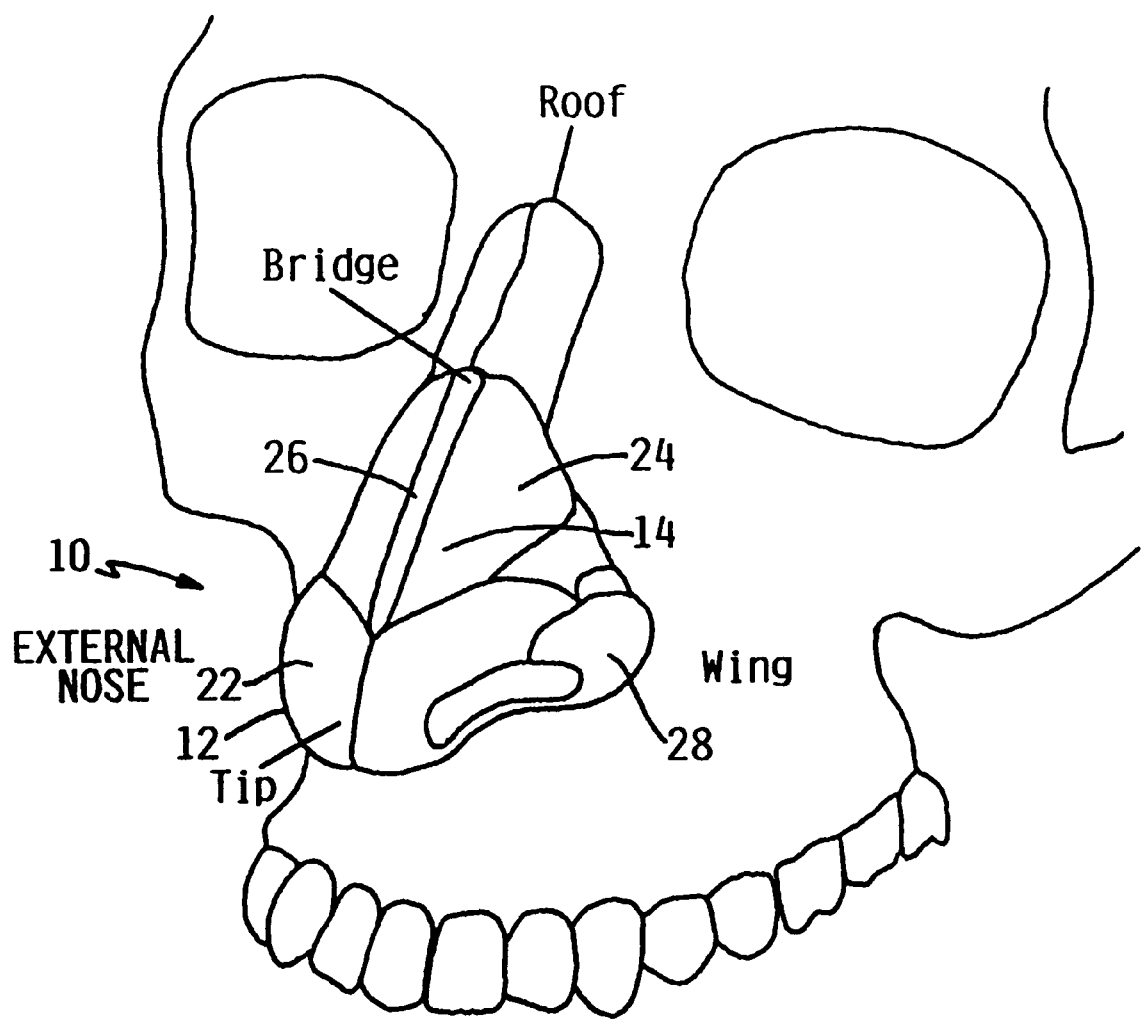
FIG. 13 is a diagrammatic illustration of the external nose.
Figure 14:
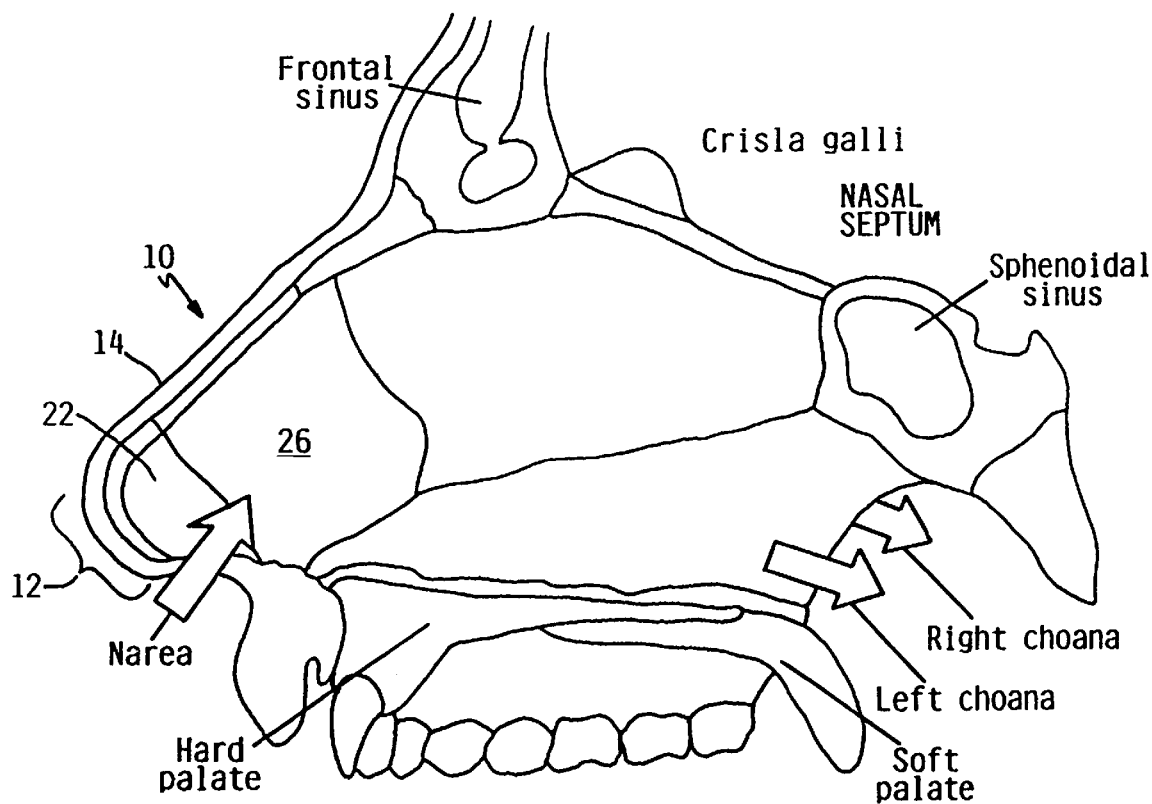
FIG. 14 is a diagrammatic illustration of the nasal septum.
Figure 15:
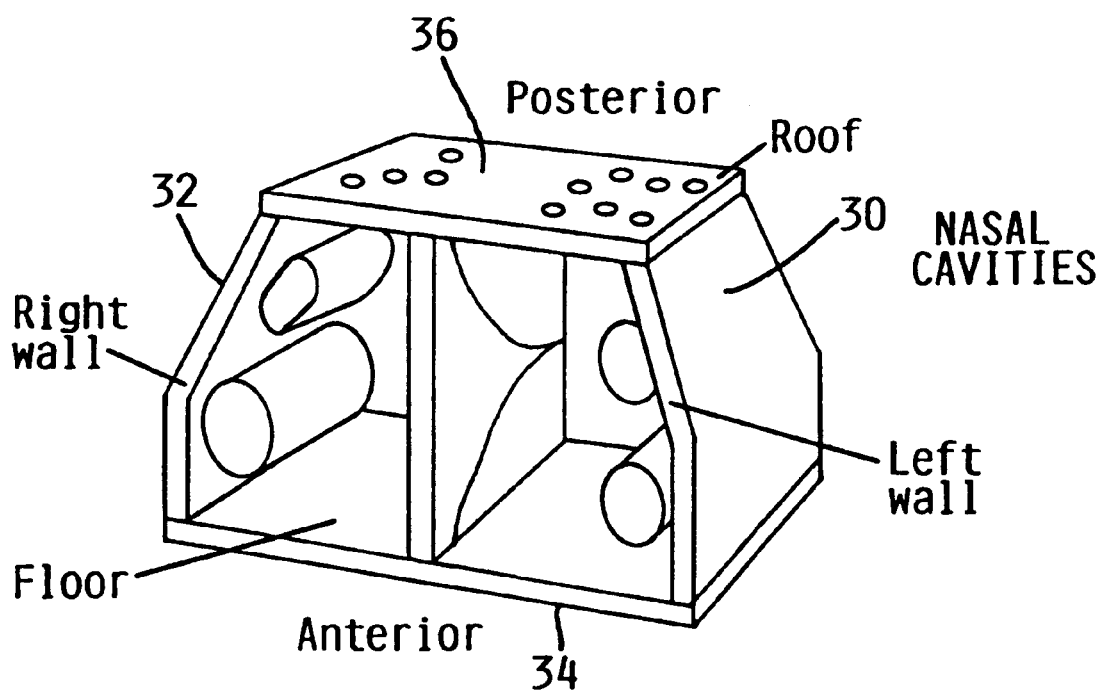
FIG. 15 is a diagrammatic illustration of the nasal cavities.

Nose structure is shown in FIGS. 13, 14, and 15. Reference numeral 10 generally indicates a nose. Nose 10 includes a tip 12 and a bridge 14. It is preferred that one end portion of the present nose foreshortener, described below, is placed on or beyond the tip 10 of the nose and the other end portion of the nose foreshortener is placed above the tip such as on the bridge 14 of the nose. Or, if desired, one end portion may be placed on skin tissue immediately on the alar cartilage 22 and the other end portion may be placed on skin tissue immediately on the lateral nasal cartilage 24 or immediately on the nasal septum cartilage 26. The bridge 14 of the nose 10 may generally be defined for the purposes of the present invention as running the length of the lateral nasal cartilage 24. The nose 10 further includes fibro-fatty tissue 28. The nose foreshortener at least shortens or compresses the alar cartilage 12. The nose foreshortener may further compress the lateral nasal cartilage 24, the nasal septum cartilage 26, and the fibro-fatty tissue 28. When one or more of such cartilage is compressed, the nasal passages dilate. More specifically, one or more of the left wall 30, right wall 32, floor 34, or roof 36 of the nasal cavities are pulled outwardly by such compressed or shortened cartilage. Further, during snoring, the nose foreshortener minimizes vibration of the fibro-fatty tissue 28 and the lateral nasal cartilage 24. As to nose structure and such cartilage, the following reference, particularly page 92, is hereby incorporated by reference in its entirety: KAPIT and ELSON, *The Anatomy Coloring Book,* 1993, Second Edition, HarperCollins College Publishers, New York.

In the Figures, a nose foreshortener, such as referred to above, is indicated in general by the reference numbers 40, 50, 60, 70, and 80.

In the Figures, one end portion of such respective nose foreshorteners, is indicated by the respective reference numbers 42, 52, 62, 72, and 82. This is the nose tip end portion or the portion to be applied on or beyond the tip of the nose. This nose tip end portion is preferably applied on or beyond the tip of the nose to get around the curvature or circumference of the tip of the nose such that when this tip end portion is being pulled by the anchoring end portion (described immediately below), this tip end portion compresses the cartilage 22 and other cartilage instead of merely pulling skin up if applied too far up the nose such as too far up the bridge of the nose.

In the Figures, the other end portion, the anchoring end portion, of such respective nose foreshorteners, is indicated by the respective reference numbers 44, 54, 64, 74, and 84. This is the anchoring end portion to be applied to the bridge of the nose.

Each of the nose foreshorteners have an outer visible face and an inner face. At least sections of the inner face on the end portions have adhesive A thereon.

Each of the nose foreshorteners further has a liner L or, more specifically, two liner portions covering the adhesive. Each of the liners or liner portions is removable from its adhesive.

FIGS. 2, 3, 4, and 6 show transversely oriented spring nasal dilators 90, 92, and 94. As to such spring nasal dilators, the Johnson U.S. Pat. No. 5,533,499 entitled Nasal Dilator and the Doubek et al. U.S. Pat. No. 5,533,503 are hereby incorporated by reference in their entireties.

Spring nasal dilators 90, 92 and 94 each have a plastic flat spring 90a, 92a, and 94a embedded therein. Flat springs 92 and 94 form substantially the shape of an inverted V when in their flat form. Each of the transverse nasal dilators have an inner adhesive face and a removable liner on such inner adhesive face.

Tip end portions 42 and 52 are integral with their transversely oriented spring nasal dilators. Such is preferred.

However, if desired, nose foreshorteners or strips 60, 70 and 80 may be used in combination with a transversely oriented spring nasal dilator, such as one of the dilators shown and described in the above referenced U.S. Pat. Nos. 5,533,499 and 5,533,503. In such a case, it is preferred that the transversely oriented spring nasal dilator is first placed on the nose and that subsequently the nose foreshortener strip is placed on the nose so as to use the exterior face of the transversely oriented nasal dilator as an anchor. Such an anchor is nonoily, unlike the skin of the nose.

As to the material for the nose foreshorteners 40, 50, 60, 70, and 80, the Johnson U.S. Pat. No. 5,533,499 entitled Nasal Dilator and the Doubek et al. U.S. Pat. No. 5,533,503 are hereby incorporated by reference in their entireties. As to the adhesive for such nose foreshorteners, the Johnson U.S. Pat. No. 5,533,499 entitled Nasal Dilator and the Doubek et al. U.S. Pat. No. 5,533,503 are hereby incorporated by reference in their entireties. As to the liners for such nose foreshorteners, the Johnson U.S. Pat. No. 5,533,499 entitled Nasal Dilator and the Doubek et al. U.S. Pat. No. 5,533,503 are hereby incorporated by reference in their entireties.

The material for such nose foreshorteners may be clear or translucent or opaque.

The adhesive for such nose foreshorteners is preferably nonallergenic.

It is preferred that the liner include two liner portions, such as two liner portions 100 and 102 separated by a score 104, shown in FIG. 5. Liner portion 102 defines the tip end portion 42 and covers adhesive on the inner face of such tip end portion 42. Liner portion 100 may cover adhesive along its entire length, but more preferably covers adhesive only at an upper portion such as a portion traversed by the transversely oriented spring nasal dilator 90. Further score lines are indicated by reference numerals 106, 108, 110, and 112. Liner portions are defined by such score lines, and the shapes of the liner portions are defined by the shapes of the nose foreshortener strips above and below these score lines.

It should be noted that the nose foreshorteners 40, 50, 60, 70, and 80 each includes a respective neck 1 14, 116, 118, 120, and 122. Each of the necks runs between the anchoring end portion and the tip end portion and includes a width less than the width of either of such end portions. It is preferred that each of the necks includes a less amount of adhesive than the end portions or a less sticky adhesive. It is more preferred that each of the necks includes no adhesive.

The present invention includes a method of applying the nose foreshortener. Such method of the present invention for foreshortening the nose uses a first strip including a pair of opposite end portions, with each of the opposite end portions having an inner face and an adhesive on at least a section of each of the inner faces of the opposite end portions. The first strip further includes a removable liner over the adhesive. The method includes the steps of a) removing the liner from the adhesive; b) pushing up the tip of a nose in a direction generally toward the eyes; c) applying one of the end portions to a position on or beyond the tip of the nose; and d) applying the other of the end portions to the bridge of the nose such that the tip of the nose is held up whereby the nose is foreshortened.

The liner may include two liner portions separated by a score, with one of the liner portions covering adhesive on one of the end portions and the other liner portion covering adhesive on the other end portion. In such a case, the step of removing the liner from the adhesive includes the steps of first removing the liner portion from the end portion to be applied to the position on or beyond the tip of the nose and then removing the other liner portion, with such latter step of then removing the other liner portion occurring after the end portion to be applied on or beyond the tip of the nose has been applied to the position on or beyond the tip of the nose.

Figure 1:
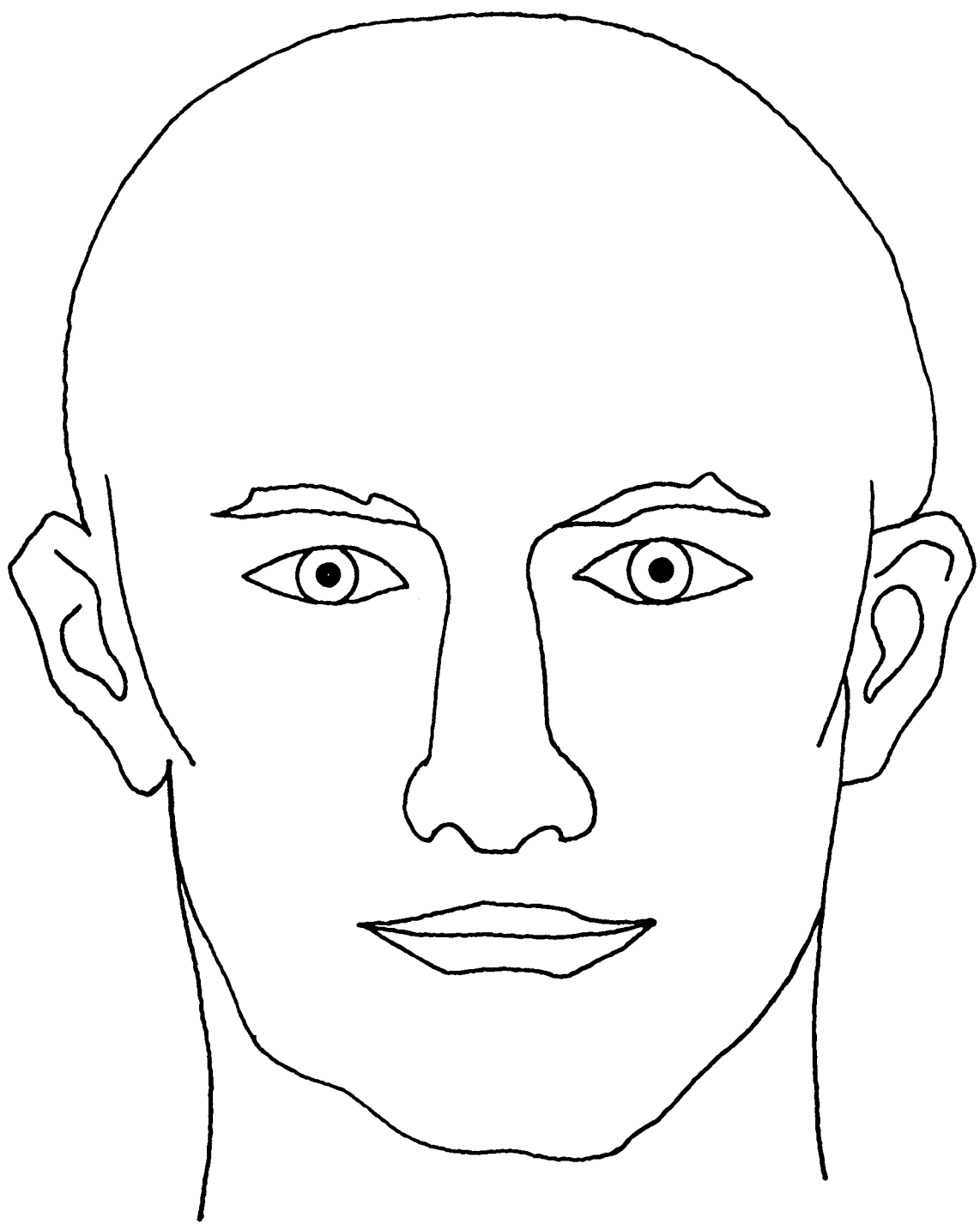
FIG. 1 shows a frontal view of a face before the present nose foreshortener is applied to the face.
Figure 2:
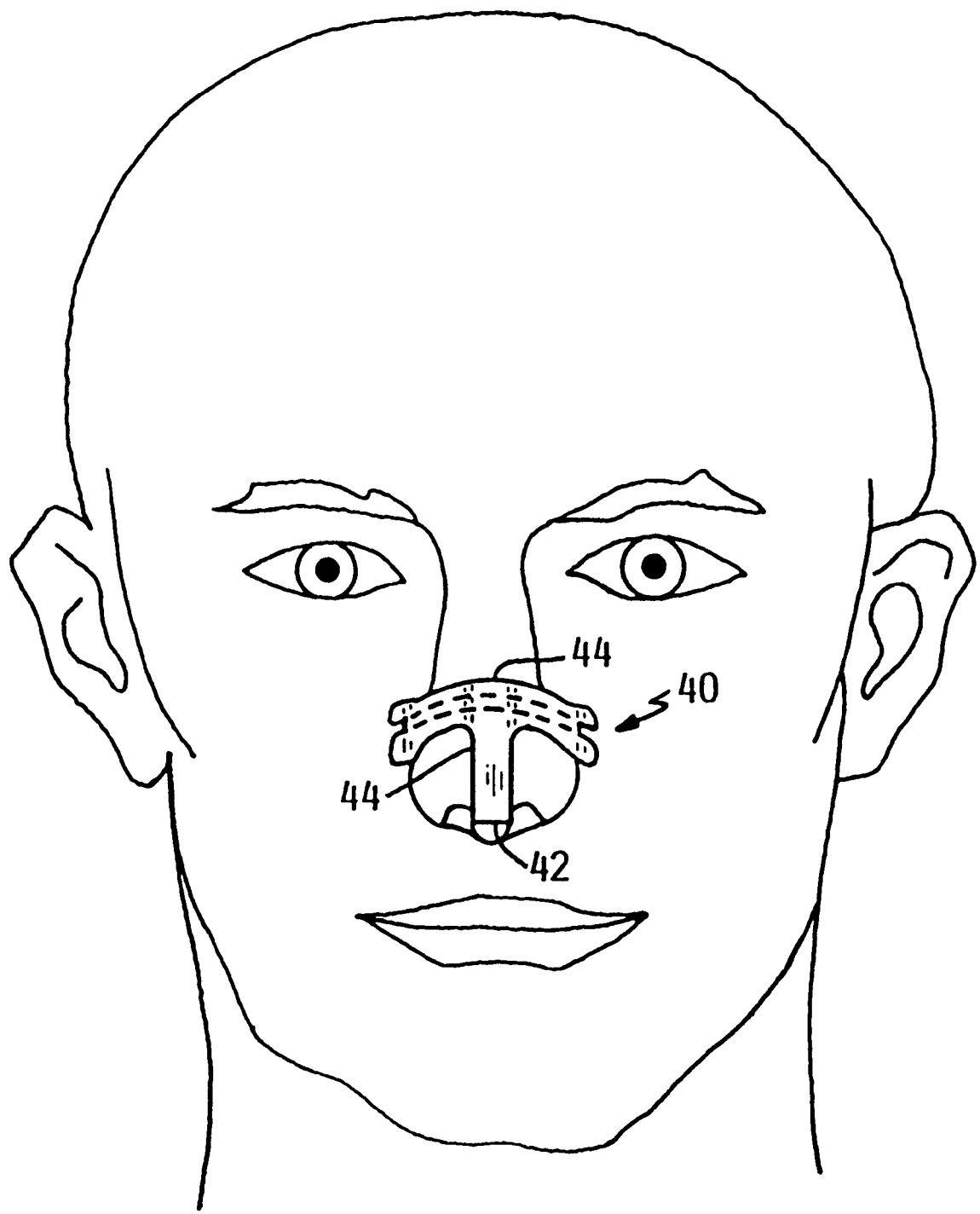
FIG. 2 shows a frontal view of the face of FIG. 1 with the present nose foreshortener applied thereto.
Figure 3:
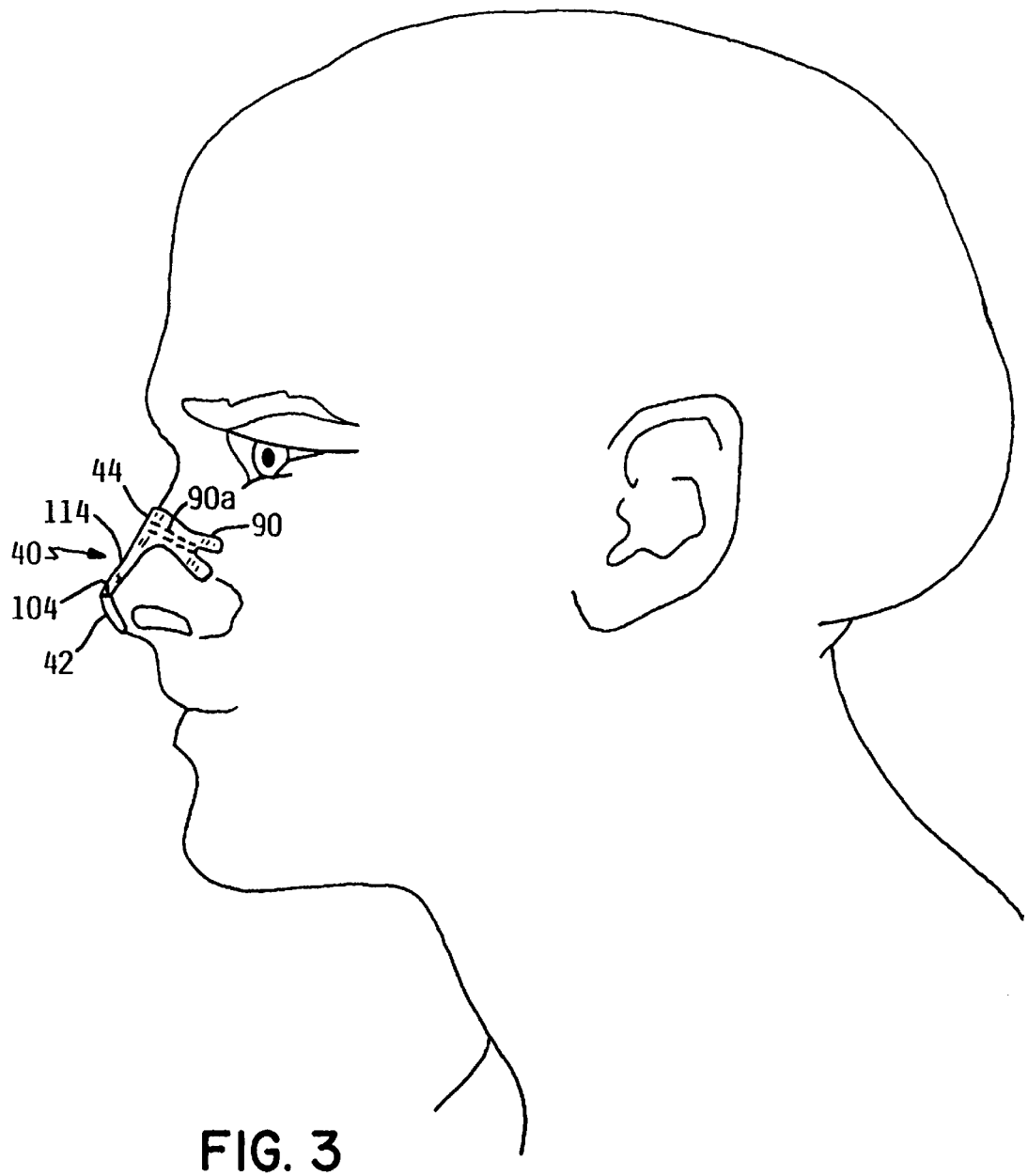
FIG. 3 shows a profile of the face of FIG. 3.
Figure 10:
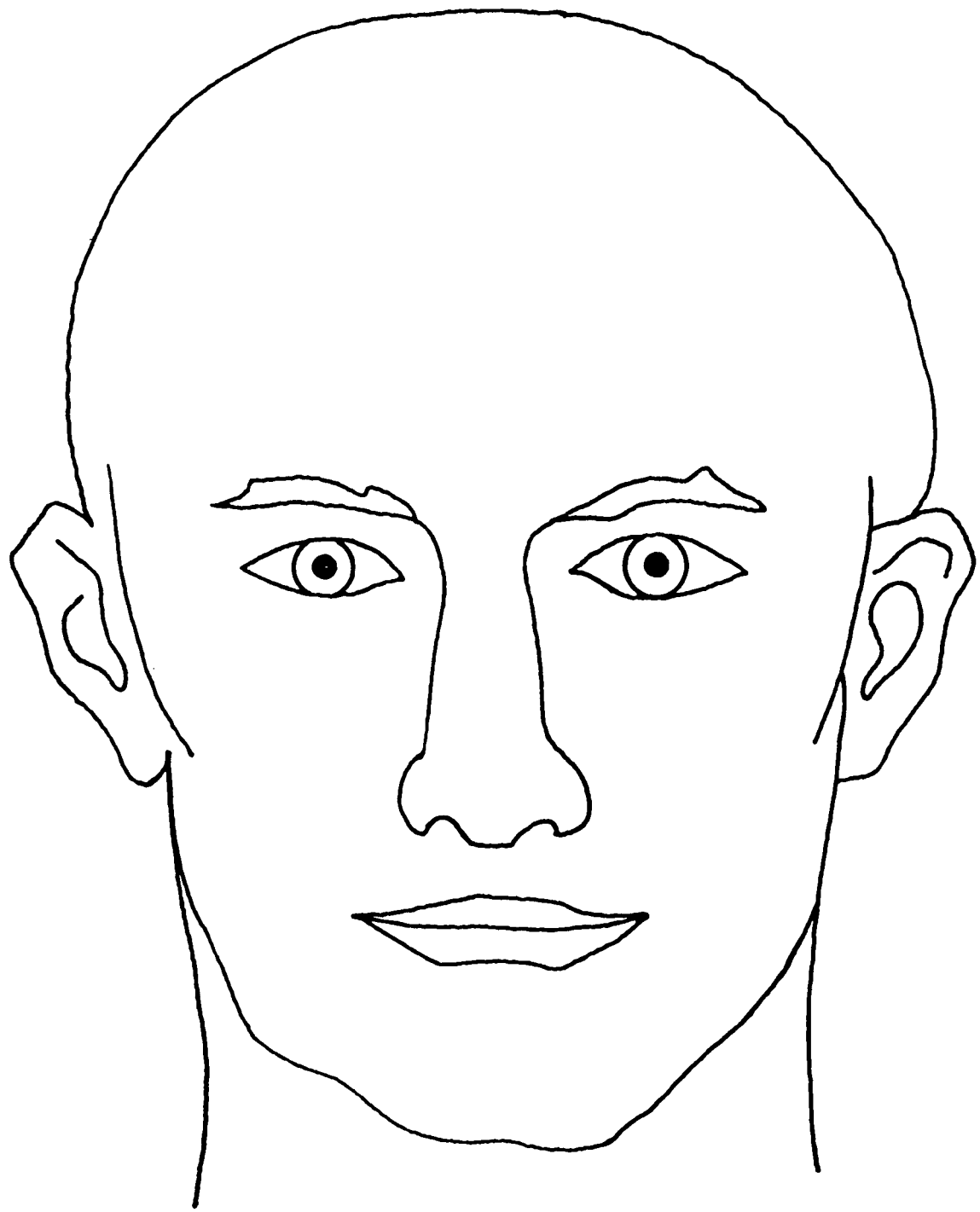
FIG. 10 shows a frontal view of a face before the nose foreshortener of FIG. 7 is applied to the face.
Figure 11:
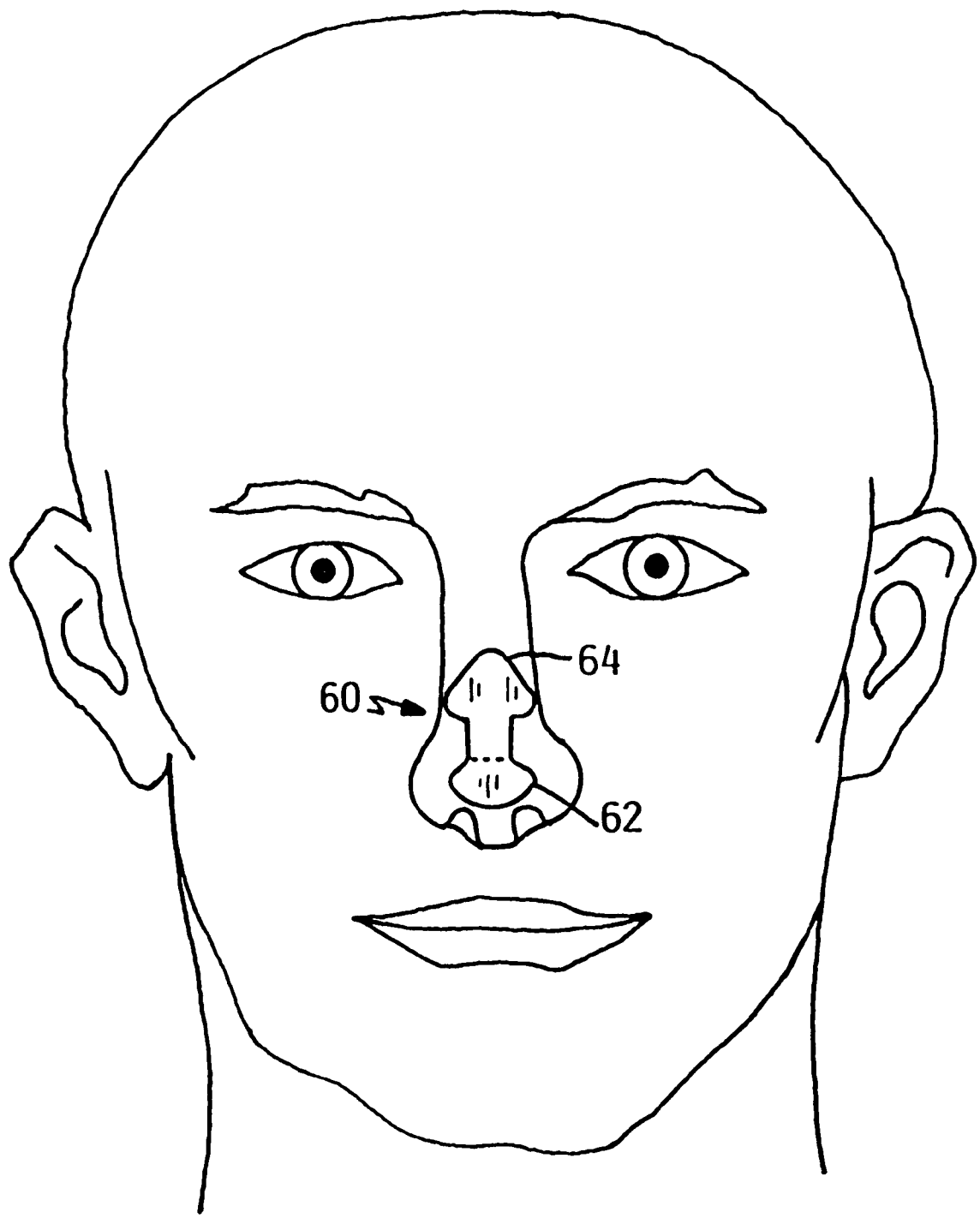
FIG. 11 shows a frontal view of the face of FIG. 10 with the nose foreshortener of FIG. 7 applied thereto.
Figure 12:
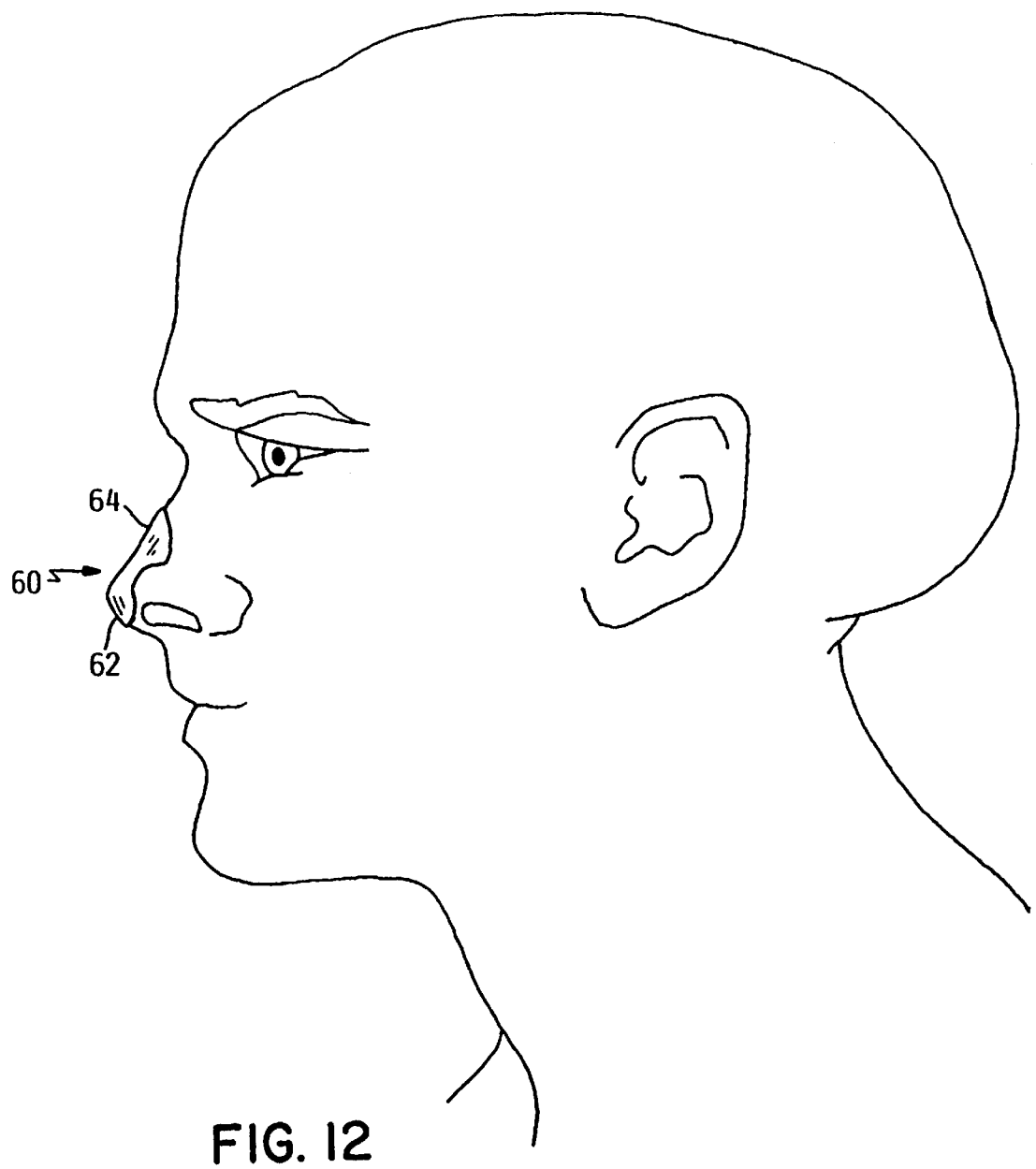
FIG. 12 shows a profile of the face of FIG. 11 having the nose foreshortener of FIG. 7 applied thereto.

FIGS. 1 and 10 shows a facial structure prior to the present nose foreshortener being applied. FIGS. 2 and 3 and FIGS. 11 and 12 show the same facial structure after the nose foreshortener has been applied. After application, in FIGS. 2 and 3 and in FIGS. 11 and 12, the nostrils of the nose have been opened upwardly and further have been dilated.

It should be noted that the present nose foreshortener is a nasal passage enlarger and straightener device. Its purpose is to assist greater volume of air in an intake of breath with less effort and reduce natural air intake blockages.

Noses have different sizes, shapes and lengths. However, most if not all noses have openings that increase in diameter when foreshortened.

When you place a finger under your nose and push up on the tip of the nose, you will find an increase in nasal passage air capacity. The improvement is to add an adhesive backed or woven or nonwoven base strip under the nasal dilators such as in the Johnson U.S. Pat. No. 5,533,499 entitled Nasal Dilator and the Doubek et al. U.S. Pat. No. 5,533,503. When applying the extension, i.e., the nose foreshortener, clean the skin between the nostrils under the nose as well as the area above the tip of the nose where the standard transversely oriented spring nasal dilator is applied. Remove the liner or liner portions from the nose foreshortener and apply the narrow strip under the nose between the nostrils. Then grasp the nose foreshortener in the top middle portion, such as at the neck, and pull up snugly to where the tip of the nose is comfortably compressed. This action will lift the tip of the nose and foreshorten the nose and compress the cartilage referred to above. Then remove the liner portion from the anchoring end portion of the nose foreshortener and apply such portion to the bridge of the nose. Then apply the integral transversely oriented nasal dilator, i.e. the second strip or the transverse strip to the right and left sides of the nose.

The present nose foreshorteners when used by itself or in conjunction with the transversely oriented spring nasal dilator permits more air to flow through the nose to the lungs thereby minimizing snoring, maximizing the volume of air flowing to the lungs, maximizing the rate of air inhaled and exhaled, and minimizing the effort needed to inhale and exhale.

It should be noted that nose foreshortener of FIG. 9 shows end portions 82 and 84 which are substantially immediately adjacent to one another. Here, the neck 122 may traverse the transition from the alar cartilage 22 to the lateral nasal cartilage 24.

It should be noted that the nose foreshortener shown in FIG. 7 has end portions 62 and 64 generally reflecting the shape of diamonds or arrowheads with three rounded points 130, 132, and 134 on one end and three rounded points 140, 142, and 144 on the other end.

If desired, transversely oriented end portion 84 may have a flat plastic spring embedded therein to function like the plastic springs in FIGS. 4 and 6.

It is preferred to space the tip end portion of the nose foreshortener from the upper lip. It is even more preferred to terminate the tip end portion at a position above the area directly between the nostrils as such an area includes tender skin. However, given such, it is preferred that the tip end portion be on or beyond the end of the nose so as to utilize the rounding of the nose for leverage for the pulling and compressing action desired by the nose foreshortener.

Figure 16:
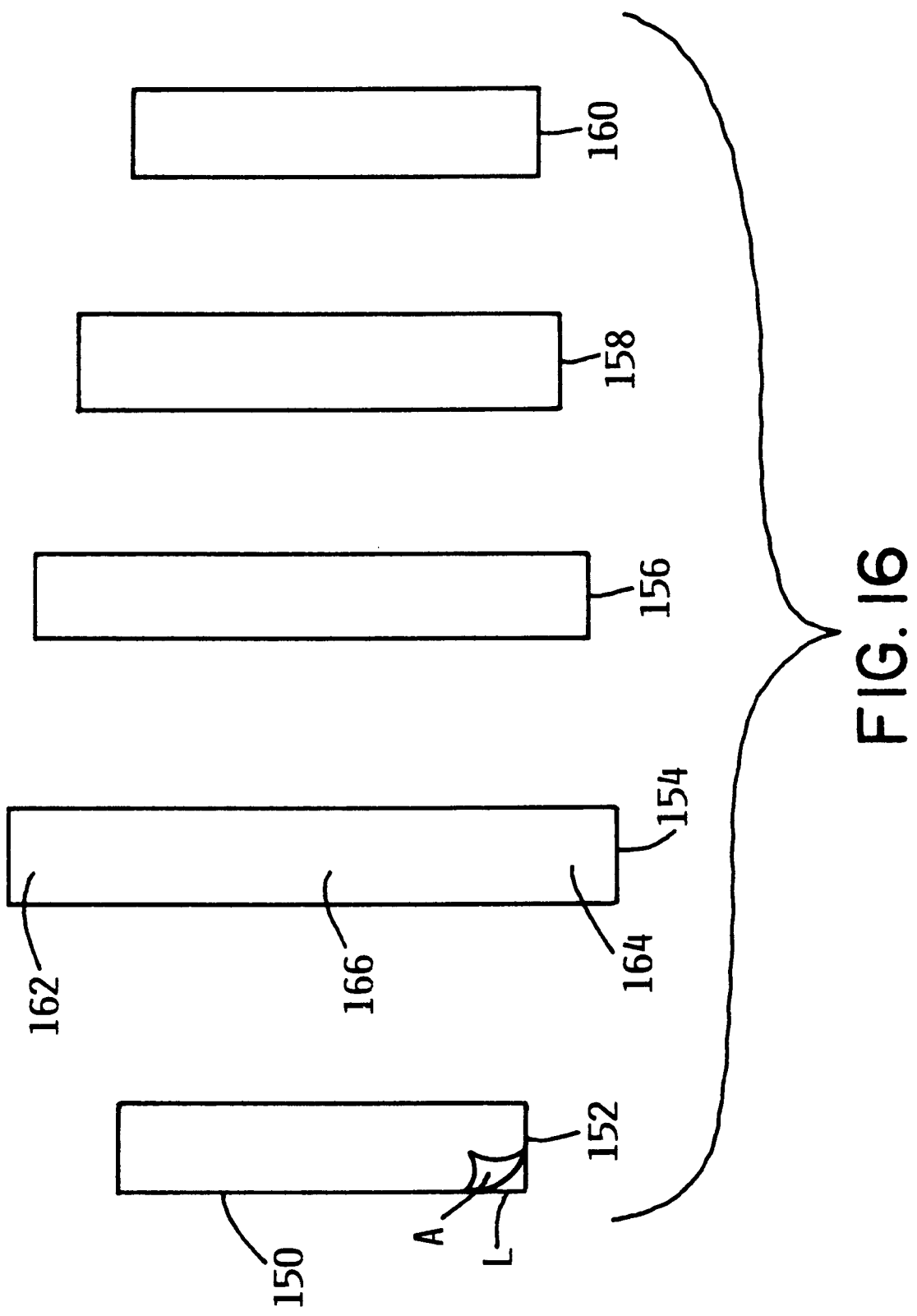
FIG. 16 shows a resiliently retracting nose foreshortening strip in an unstretched configuration, a stretched configuration, a retracting configuration, a further retracting configuration and a fully retracted configuration.

FIG. 16 shows a resiliently retracting nose foreshortener strip 150 in an unstretched configuration 152, a stretched configuration 154, a retracting configuration 156, a further retracting configuration 158 and a fully retracted configuration 160. Strip 150 is similar to anyone of the strips 50, 60, 70 and 80 (shown in FIGS. 6, 7, 8 and 9) except that strip 150 is formed of a material that is resiliently retracting. Like such strips 50, 60, 70, and 80, strip 150 includes an adhesive A on an inner face. Such adhesive is covered by a liner L which is peeled off prior to stretching the strip 150.

Strip 150 includes opposing end portions 162 and 164 and a medial portion 166. The entire strip 150, including opposing end portions 162, 164 and medial portion 166, is preferably formed of a resiliently retracting material. However, if desired, only the medial portion 166 or a section of the medial portion 166 may be formed of a resiliently retracting material. Further, if desired, medial portion 166 may be void of adhesive or have an adhesive of a lesser strength.

More specifically, the nature of the resiliently retracting material is preferably such that, when stretched, recovers to its original length when the stretching force is relaxed or released. When one of the opposing end portions 162 or 164 is adhered or anchored at one portion of the nose, and the strip 150 is then stretched and the other opposing end portion 162 or 164 is anchored at another portion of the nose, the strip 150 will provide a constant pulling action or constant drawing action where such two nose portions are continuously being drawn together. Such two nose portions may be the tip of the nose and a portion of the bridge of the nose where the strip 150 acts as a nose foreshortener or such two nose portions may be respective side portions of the nose where such strip 150 acts as a transverse strip. Where placed transversely across the nose and anchored on the sides of the nose, strip 150 critically does not include any springs or rods that apply a force in a direction out of the face of its respective nasal strip. In contrast, the force provided by strip 150 is lengthwise or longitudinal such that the opposing end portions 162 and 164 are drawn together with an equal force after being stretched.

It should be noted that the resilient force provided by the strip 150 so as to the draw the opposing end portions 162 and 164 together longitudinally together, works to draw the skin and underlying tissue in a generally outwardly direction which is somewhat oblique because of the pulling in the longitudinal direction. Further, such a force works to stabilize the underlying tissue. This underlying tissue may otherwise tend to be drawn inwardly when one breathes through his or her nose which is undesirable.

It should be noted that the degree of stretch and resilient retraction shown in FIG. 16 may not reflect the actual degree of stretch and retraction.

FIG. 17 shows a strip 170 that is preferably placed transversely across the bridge of the nose. Like strip 150, strip 170 is resiliently retracting. Reference number 172 indicates an initial unstretched configuration, reference number 174 indicates a fully stretch configuration, reference number 176 indicates a resiliently retracting configuration, and reference number 178 indicates a fully retracted configuration. Again, the actual degree of stretch and resilient retraction is preferably less than that indicated in FIG. 17.

Strip 170 includes a liner L formed in the shape of the strip 172. Liner L covers the skin friendly adhesive A. Liner L is preferably not resilient in the longitudinal direction.

Strip 170 includes a pair of end extensions 180 and 182 on each end portion of the strip. End extension 180 is slightly longer and it is preferred that such end extension 180 is engaged via the adhesive A to the flare of a nostril, with the shorter end extension 182 on the skin of the face or face or on the skin of the side of the nose.

Strip 170 includes a medial portion 184 that may or may not have adhesive. Preferably such a medial portion 184 is void of adhesive.

While strip 150 may serve as either a vertically extending nasal dilator (i.e. a nose foreshortener) or a horizontally extending nasal dilator, and while strip 170 may also serve as either a vertically or horizontally extending nasal dilator, strip 170 is preferably used as a horizontally extending nasal dilator.

Strip 150 pulls the nasal cavity on the sides of the nose when across the nose transversely and pulls equally on the tissue on either side of the nose. Again, this pulling is somewhat obliquely because of the longitudinal resilient retraction; however, in the perspective of the tissue which is being pulled, the pulling is generally outwardly. Further, such an oblique outward pulling nevertheless stabilizes the underlying tissue, minimizing the tendency of the underlying tissue to be drawn in when one breathes.

FIGS. 18A to 18D show a combination strip 190 having a horizontally or transversely extending nasal dilator portion 192 and a vertically extending (nose foreshortener) nasal dilator portion 194. Combination strip 190 includes a liner L for lining the face of strip 190 that includes adhesive A.

Combination strip 190 is resiliently retracting. FIG. 18A shows an unstretched initial configuration, FIG. 18B shows the fully stretched configuration, FIG. 18C shows the strip 190 resiliently retracting, and FIG. 18D shows the strip 190 in the fully retracted form. The fully retracted form shown in FIG. 18D is of a size preferably identical to the initial size shown in FIG. 18A.

It should be noted that each of the strips 150, 170 and 190 retract close to their initial size and, more preferably, retract exactly to their initial size when stretched by hand and before being placed on the nose. Of course, when on the nose, it is preferred that the strips 150, 170, and 190 are applied when in the stretched position such that a constant pulling action is applied by the ends of such strips 150, 170 and 190 when engaged on the nose. Further, when on the nose, it is preferred that the resilient material has a sufficient resiliency to provide a constant pulling action, but not so much resiliency that the underlying tissue is pulled apart so as to cause tissue damage or internal bleeding to the tissues. It is further preferred that the adhesive strength of the strips 150, 170 and 190 be of greater strength than the strength of the resiliency of the strip material such that the strips 150, 170 and 190 remain on the nose.

It should be noted that some materials stretch and break. Other materials stretch and remain in their stretched configuration with no bias to return to or even toward the original unstretched configuration. Still other materials stretch and slightly retract, but do not retract to their original nonstretched configuration. Yet other materials stretch and resiliently retract to their original nonstretched configuration. These latter materials are most preferred for strips 150, 170, and 190. An example of such a material is a rubber or elastomeric material or a rubber based or elastomeric based material.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

What is claimed is:

1. An externally applied nasal dilator for tightening and thus stabilizing nasal passages, comprising, in combination:

a) a first strip comprising a pair of opposite end portions and a medial portion between the opposite end portions, with each of the opposite end portions having an inner face, with the first strip having lateral and longitudinal directions;

b) an adhesive on at least a section of each of the inner faces of the opposite end portions wherein one of the end portions adheres on a first portion of the nose and wherein the other of the end portions adheres on a second portion of the nose; and c) wherein at least a section of the medial portion is resilient in the longitudinal direction to draw the opposite end portions toward each other after the opposite end portions have been stretched apart, wherein the first strip is stretched and the opposite end portions are adhered to the first and second portions of the nose, wherein after said opposite end portions are adhered to the first and second portions of the nose the first strip resiliently retracts via the medial portion to tighten and thus stabilize underlying tissue so as to stabilize nasal passages.

2. The externally applied nasal dilator according to claim 1, and further comprising a second strip engaged to the first strip, with the first and second strips being transverse of the other, with the second strip also comprising a pair of opposite end portions and a medial portion between the opposite end portions, with each of said opposite end portions of the second face having an inner face, with the second strip having lateral and longitudinal directions, with adhesive being on at least a section of each of the inner faces of the opposite end portions of the second strip, and with at least a section of the medial portion of the second strip being resilient in the longitudinal direction of the second strip to draw said opposite end portions of the second strip toward each other after said opposite end portions have been stretched apart, wherein the second strip is stretched and the opposite end portions of the second strip are adhered to third and fourth portions of the nose, wherein after said opposite end portions of the second strip are adhered to the third and fourth portions of the nose the second strip resiliently retracts via said medial portion of the second strip to tighten and thus stabilize underlying tissue so as to stabilize nasal passages.

3. The externally applied nasal dilator according to claim 2 wherein the first and second strips are integral with one another.

4. A method of applying the nasal dilator to the nose, with the nasal dilator being an externally applied nasal dilator for tightening and thus stabilizing nasal passages, with the nasal dilator comprising: a) a first strip comprising a pair of opposite end portions and a medial portion between the opposite end portions, with each of the opposite end portions having an inner face, with the first strip having lateral and longitudinal directions; b) an adhesive on at least a section of each of the inner faces of the opposite end portions wherein one of the end portions adheres on a first portion of the nose and wherein the other of the end portions adheres on a second portion of the nose; and c) wherein at least a section of the medial portion is resilient in the longitudinal direction to draw the opposite end portions toward each other after the opposite end portions have been stretched apart, wherein the first strip is stretched and the opposite end portions are adhered to the first and second portions of the nose, wherein after said opposite end portions are adhered to the first and second portions of the nose the first strip resiliently retracts via the medial portion to tighten and thus stabilize underlying tissue so as to stabilize nasal passages; with the method comprising the steps of:

a) stretching the first strip;

b) applying one end portion to a portion of the tip of the nose between the nostrils;

c) applying the other end portion to a portion of the bridge of the nose; and d) resiliently retracting the first strip wherein after said opposite end portions are adhered to the tip and bridge portions of the nose the first strip resiliently retracts via the medial portion to tighten and thus stabilize underlying tissue so as to stabilize nasal passages and whereby the first strip is applied to extend generally vertically on the nose.

5. A method of applying the nasal dilator to the nose, with the nasal dilator being an externally applied nasal dilator for tightening and thus stabilizing nasal passages, with the nasal dilator comprising: a) a first strip comprising a pair of opposite end portions and a medial portion between the opposite end portions, with each of the opposite end portions having an inner face, with the first strip having lateral and longitudinal directions; b) an adhesive on at least a section of each of the inner faces of the opposite end portions wherein one of the end portions adheres on a first portion of the nose and wherein the other of the end portions adheres on a second portion of the nose; and c) wherein at least a section of the medial portion is resilient in the longitudinal direction to draw the opposite end portions toward each other after the opposite end portions have been stretched apart, wherein the first strip is stretched and the opposite end portions are adhered to the first and second portions of the nose, wherein after said opposite end portions are adhered to the first and second portions of the nose the first strip resiliently retracts via the medial portion to tighten and thus stabilize underlying tissue so as to stabilize nasal passages; with the method comprising the steps of:

a) stretching the first strip;

b) applying one end portion to a portion of one side of the nose;

c) applying the other end portion to a portion of the other side of the nose, with the bridge of the nose being between the end portions adhering on the sides of the nose: and d) resiliently retracting the first strip wherein after said opposite end portions are adhered to the sides of the nose the first strip resiliently retracts via the medial portion to tighten and thus stabilize underlying tissue so as to stabilize nasal passages whereby the first strip is applied to extend transversely on the nose.

6. The externally applied nasal dilator according to claim 1, wherein the opposite end portions are resiliently retractable after the opposite end portions are adhered to the first and second portions of the nose and wherein the medial portion is resiliently retractable after the opposite end portions are adhered to the first and second portions of the nose.

7. The externally applied nasal dilator according to claim 1 wherein at least a section of the medial portion of the first strip is void of adhesive.

8. The externally applied nasal dilator according to claim 1 wherein the first strip includes a first configuration where the first strip is nonstretched and in a stand alone configuration, wherein the first strip includes a second configuration where the first strip is stretched and in a stand alone configuration, wherein the first strip includes a third configuration where the strip resiliently recovers from the second configuration to the first configuration, with the first and third configurations having a same length, and wherein the second configuration provides a pulling force on the skin of the nose sufficiently great to maximize a stabilization of underlying nasal tissue and sufficiently small to minimize damage to nasal tissue.

9. The externally applied nasal dilator according to claim 1 wherein the first strip comprises a rubber or elastomer.

10. The externally applied nasal dilator according to claim 1 wherein the first strip comprises a rubber based or elastomer based material.

11. An externally applied nasal dilator for tightening and thus stabalizing nasal passages and being applied transversely across the bridge of a nose, with the bridge of the nose being between two sides of the nose, comprising, in combination:
   a) a first strip comprising a pair of opposite end portions and a medial portion between the opposite end portions, with each of the opposite end portions having an inner face, with the first strip having lateral and longitudinal directions;
   b) an adhesive on at least a section of each of the inner faces of the opposite end portions wherein one of the end portions adheres on a first side of the nose and wherein the other of the end portions adheres on a second side of the nose to dispose the medial portion over the of the nose; and
   c) wherein at least a section of the medial portion is resilient in the longitudinal direction to draw the opposite end portions toward each other after the opposite end portions have been stretched apart, wherein the first strip is stretched and the opposite end portions are adhered to the first and second sides of the nose, wherein after said opposite end portions are adhered to the first and second sides of the nose the first strip resiliently retracts via the medial portion to tighten and thus stabalize underlying tissue so as to stabalize nasal passages.

12. The externally applied nasal dilator according to claim 11 wherein the first strip includes a first configuration where the first strip is nonstretched and in a stand alone configuration, wherein the first strip includes a second configuration where the first strip is stretched and in a stand alone configuration, wherein the first strip includes a third configuration where the strip resiliently recovers from the second configuration to the first configuration, with the first and third configurations having a same length, and wherein the second configuration provides a pulling force on the skin of the nose sufficiently great to maximize a stabilization of underlying nasal tissue and sufficiently small to minimize damage to nasal tissue.

13. An externally applied nasal dilator for tightening and thus stabilizing nasal passages and being applied to the tip of the nose and the bridge of the nose, comprising, in combination:
   a) a first strip comprising a pair of opposite end portions and a medial portion between the opposite end portions, with each of the opposite end portions having an inner face, with the first strip having lateral and longitudinal directions;
   b) an adhesive on at least a section of each of the inner faces of the opposite end portions wherein one of the end portions adheres on the tip of the nose and wherein the other of the end portions adheres on a portion of the bridge of the nose; and
   c) wherein at least a section of the medial portion is resilient in the longitudinal direction to draw the opposite end portions toward each other after the opposite end portions have been stretched apart, wherein the first strip is stretched and the opposite end portions are adhered to the tip of the nose and the portion of the bridge of the nose, wherein after said opposite end portions are adhered to the tip of the nose and the portion of the bridge of the nose the first strip resiliently retracts via the medial portion to tighten and thus stabilize underlying tissue so as to stabilize nasal passages.

14. The externally applied nasal dilator according to claim 13 wherein the first strip includes a first configuration where the first strip is nonstretched and in a stand alone configuration, wherein the first strip includes a second configuration where the first strip is stretched and in a stand alone configuration, wherein the first strip includes a third configuration where the strip resiliently recovers from the second configuration to the first configuration, with the first and third configurations having a same length, and wherein the second configuration provides a pulling force on the skin of the nose sufficiently great to maximize a stabilization of underlying nasal tissue and sufficiently small to minimize damage to nasal tissue.

15. The externally applied nasal dilator according to claim 11 wherein the first strip includes a first configuration where the first strip is nonstretched and in a stand alone configuration, wherein the first strip includes a second configuration where the first strip is stretched and in a stand alone configuration, wherein the first strip includes a third configuration where the strip resiliently recovers partially from the second configuration to the first configuration.

16. The externally applied nasal dilator according to claim 13 wherein the first strip includes a first configuration where the first strip is nonstretched and in a stand alone configuration, wherein the first strip includes a second configuration where the first strip is stretched and in a stand alone configuration, wherein the first strip includes a third configuration where the strip resiliently recovers partially from the second configuration to the first configuration.

* * * * *